US00PP31428P2

(12) United States Plant Patent
Van der Knaap

(10) Patent No.: US PP31,428 P2
(45) Date of Patent: Feb. 4, 2020

(54) ***FICUS* PLANT NAMED 'BAMBINO2'**

(50) Latin Name: *Ficus lyrata*
Varietal Denomination: BAMBINO2

(71) Applicant: Eduard J. M. Van der Knaap, Bleiswijk (NL)

(72) Inventor: Eduard J. M. Van der Knaap, Bleiswijk (NL)

( * ) Notice: Subject to any disclaimer, the term of this patent is extended or adjusted under 35 U.S.C. 154(b) by 0 days.

(21) Appl. No.: 16/350,733

(22) Filed: Dec. 27, 2018

(30) Foreign Application Priority Data

Oct. 9, 2018 (QZ) ..... PBR 2018/2549

(51) Int. Cl.
*A01H 5/00* (2018.01)

(52) U.S. Cl.
USPC ..... Plt./211

(58) Field of Classification Search
USPC ..... Plt./211
CPC ..... A01H 5/00
See application file for complete search history.

*Primary Examiner* — Annette H Para
(74) *Attorney, Agent, or Firm* — Samuel R. McCoy, Jr.

(57) ABSTRACT

A new and distinct variety of *Ficus* plant named 'BAMBINO2' which is characterized by the combination of a compact growth habit, an abundance of relatively small, cupped foliage which is dark green and glossy, and the stability of all characteristics from generation to generation.

3 Drawing Sheets

Latin name of the genus and species: The Latin name of the genus and species of the novel variety disclosed herein is *Ficus lyrata.*

Variety denomination: The inventive variety of *Ficus* disclosed herein has been given the variety denomination 'BAMBINO2'.

CROSS REFERENCE TO RELATED APPLICATIONS

This application claims priority to the Community Plant Variety Rights application number 2018/2549 filed Oct. 8, 2018 which is herein incorporated by reference.

BACKGROUND OF THE INVENTION

Parentage: 'BAMBINO2' originated as a naturally occurring, whole-plant mutation of *Ficus* 'Bambino' (U.S. Pat. No. PP9,323). In February of 2018, the inventor discovered the mutation at his commercial greenhouse in Bleiswijk, the Netherlands, growing amongst a cultivated population of 'Bambino' plants. The mutation was noted for its compact habit and relatively small, cupped foliage and was subsequently isolated for further evaluation in order to confirm the distinctness and stability of the characteristics first observed. Upon confirmation of distinctness and stability, 'BAMBINO2' was selected for commercialization in May of 2018.

Asexual Reproduction: Asexual reproduction of 'BAMBINO2', by way of stem cuttings, was first initiated in July of 2018 in at a commercial greenhouse in Lochristi, Belgium. 'BAMBINO2' was subsequently propagated by way of meristematic tissue culture. Through two subsequent generations, the unique features of this cultivar have proven to be stable and true to type.

SUMMARY OF THE INVENTION

The cultivar 'BAMBINO2' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'BAMBINO2'. These characteristics in combination distinguish 'BAMBINO2' as a new and distinct *Ficus* cultivar:

1. *Ficus* 'BAMBINO2' exhibits a compact growth habit with relatively short internodal spacing; and
2. *Ficus* 'BAMBINO2' exhibits an abundance of relatively small, cupped leaves; and
3. *Ficus* 'BAMBINO2' exhibits dark green, glossy leaves with an obovate to broad obovate shape.

BOTANICAL DESCRIPTION OF THE PLANT

Figure 1:
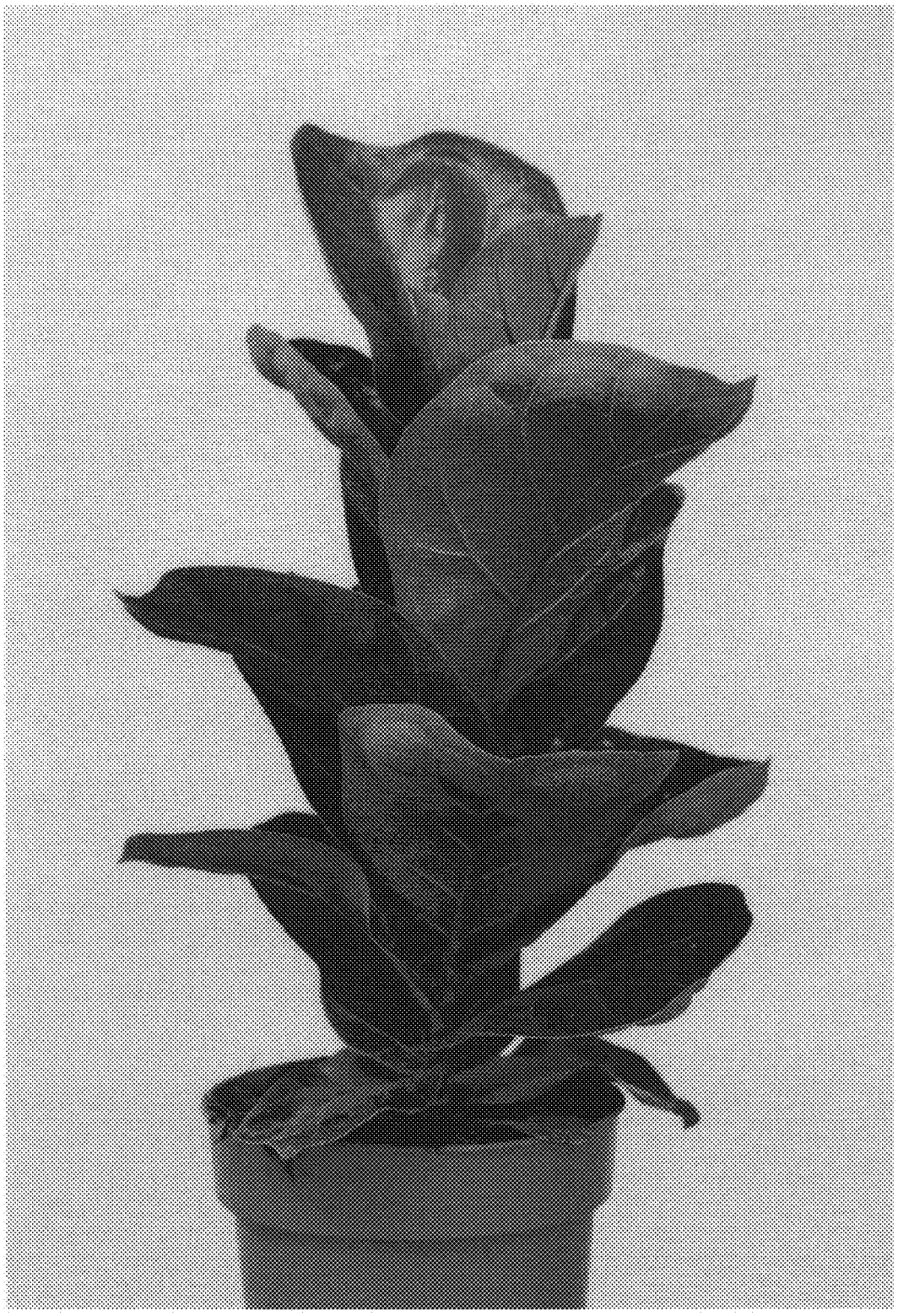
FIG. 1 illustrates, as nearly true as it is reasonably possible to make the same in color photographs of this type, an exemplary plant of 'BAMBINO2' grown in a grown in a commercial greenhouse in Bleiswijk, The Netherlands. This plant is approximately 12 months old, shown planted in a 13 cm container.
Figure 2:
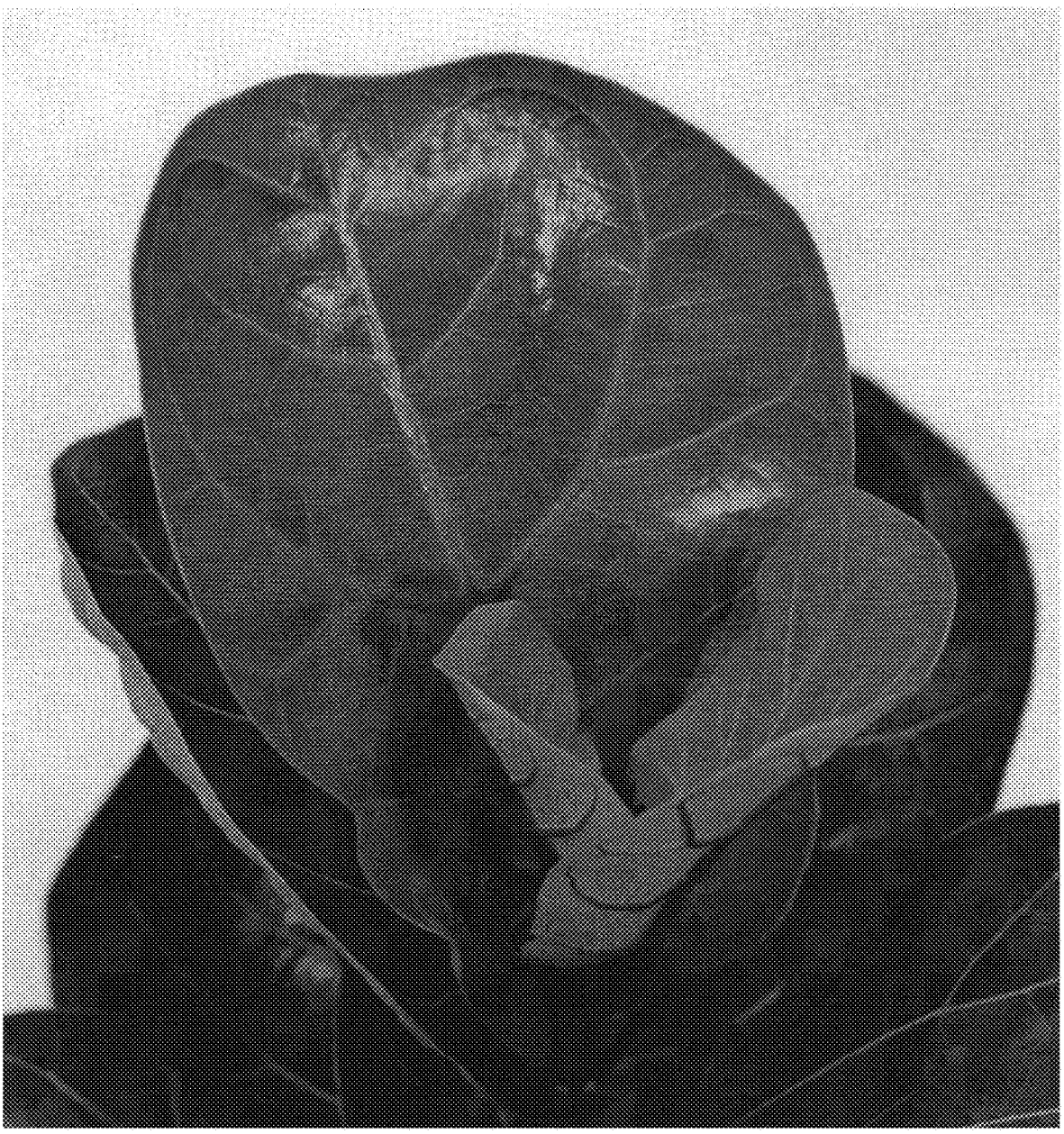
FIG. 2 illustrates, as nearly true as it is reasonably possible to make the same in color photographs of this type, the typical juvenile foliage of 'BAMBINO2'.
Figure 3:
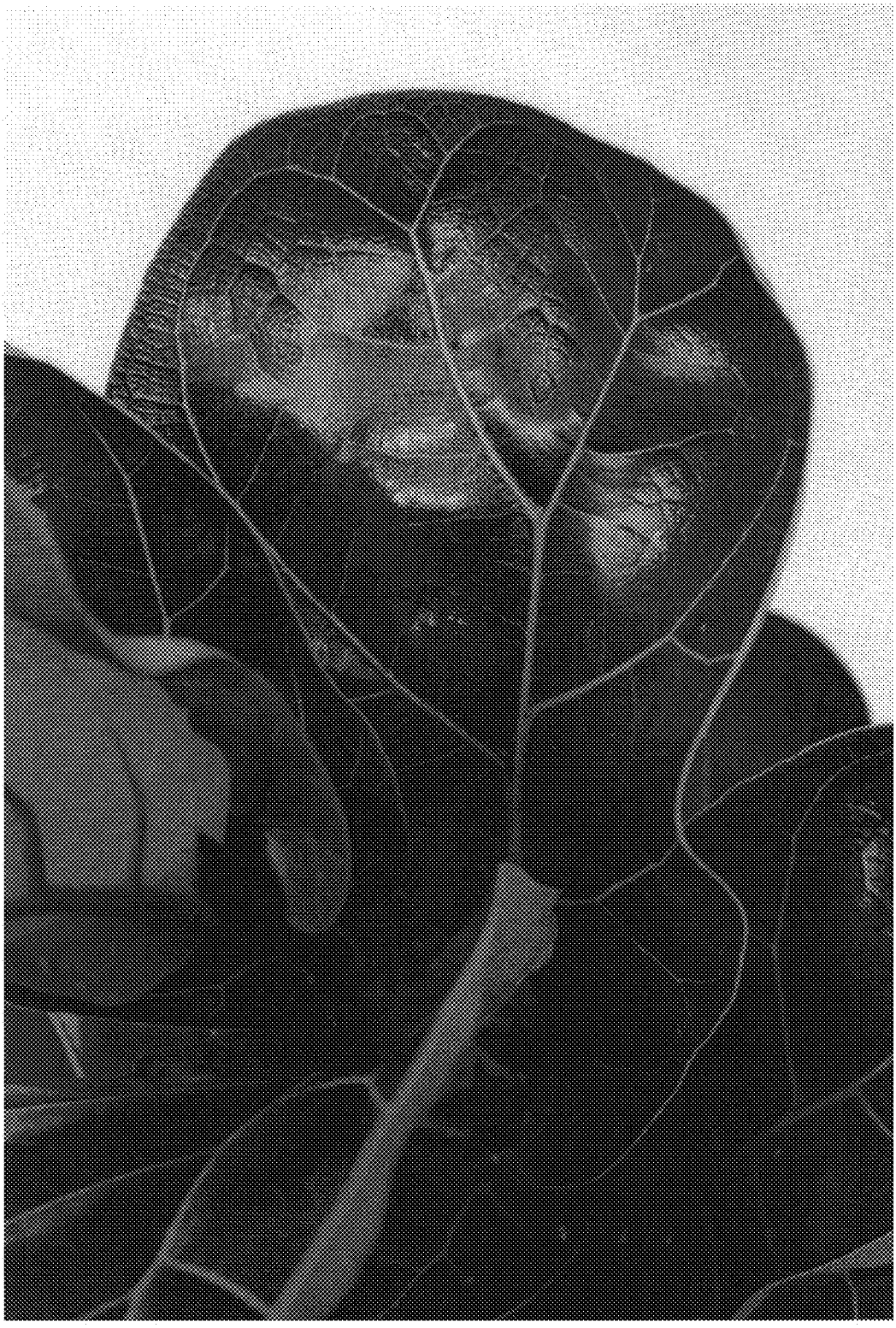
FIG. 3 illustrates, as nearly true as it is reasonably possible to make the same in color photographs of this type, the typical mature foliage of 'BAMBINO2'.

The following observations and measurements were made in October of 2018 and describe a sample set of six 12 month-old 'BAMBINO2' plants grown in 13 cm nursery pots at a plant nursery in Bleiswijk, The Netherlands. Plants were produced using conventional greenhouse production protocols for *Ficus* which consisted of shading as needed to prevent overexposure, overhead irrigation, ebb and flood irrigation tables, fertigation applications as needed, and insecticide applications for the control of thrips, spider mites and plant louse.

Those skilled in the art will appreciate that certain characteristics will vary with older or, conversely, with younger plants. 'BAMBINO2' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2015 (sixth edition).

A botanical description of 'BAMBINO2' and comparisons with the parent plant and most similar commercial variety of *Ficus* are provided below.

Plant description:

*Growth habit.*—Upright perennial.

*Plant form.*—Broad oblong.

*Average height.*—30.3 cm from the soil level to the top of the foliar plane.

*Plant spread.*—Average of 23.0 cm.

*Growth rate.*—Moderately fast.

*Plant vigor.*—Moderately vigorous.

*Propagation type.*—Stem cuttings and meristematic tissue culture propagation.

*Time to produce a rooted cutting.*—Approximately 3 to 5 weeks to produce a rooted cutting at approximately 22 degrees Celsius.

*Time to produce a finished plant.*—Approximately 18 to 22 weeks to produce a marketable finished plant.

*Disease resistance.*—Neither resistance nor susceptibility to typical *Ficus* pests and diseases has been observed.

*Environmental tolerances.*—Adapt to, at least, USDA Zones 10 through 13 and temperatures as high as 40 degrees Celsius; moderate to high tolerance to rain; moderate tolerance to wind.

Root System:

*General.*—Moderately dense and sparsely to moderately branched rooting; roots are slightly fibrous.

*Distribution in the soil profile.*—Shallow to moderately deep.

*Diameter of roots.*—0.15 cm on average.

*Texture.*—Smooth; no root hairs.

*Color.*—Greyed-yellow, nearest to RHS 162A.

Stem:

*General branching habit.*—Basally branching main stems; no lateral branching. Pinching isn't required but will improve branching.

*Length of main stems.*—Approximately 19.6 cm.

*Diameter of main stems.*—Approximately 0.7 cm.

*Internode length.*—Approximately 1.8 cm.

*Attitude.*—Near vertical.

*Cross-section.*—Rounded.

*Texture.*—Sparsely covered with lenticels; lenticels are approximately 0.1 cm long and 0.05 cm wide and are colored yellow-green, RHS 153D.

*Luster.*—Matte.

*Strength.*—Strong.

*Color, juvenile.*—Yellow-green, nearest to RHS 151A.

*Color, mature.*—Green, nearest to RHS 137B.

*Color at internodes.*—Green, nearest to RHS 137B.

Foliage:

*Arrangement.*—Alternate.

*Division.*—Simple.

*Quantity.*—14 leaves per stem.

*Attitude.*—Upward at an average angle of 30 degrees to the stem.

*Lamina.*—Shape — Obovate to broad obovate. Aspect — Moderately concave; cupped. Dimensions — 14.1 cm long and 10.4 cm wide. Apex — Bluntly apiculate to broad, undeeply emarginate. Base — Truncate. Margin — Entire, very slightly angulate; coarsely undulate. Texture of top surface — Smooth, glabrous, and very glossy. Texture of bottom surface — Smooth, glabrous, and matte. Color — Juvenile foliage, adaxial surface — Nearest to in between green and yellow-green, RHS 143A and 144A. Juvenile foliage, abaxial surface — Yellow-green, nearest to RHS 144A. Mature foliage, adaxial surface — Dark green, nearest to in between RHS NN137A and 139A. Mature foliage, abaxial surface — Green, nearest to a mixture of RHS 143B and 143C. Venation — Pattern — Pinnate. Color — Juvenile foliage, adaxial surface — Greyed-brown, nearest to in between RHS 199A and N199C. Juvenile foliage, adaxial surface — Greyed-brown, nearest to in between RHS 199A and N199C. Mature foliage, adaxial surface — Yellow-green, nearest to RHS 148A. Mature foliage, adaxial surface — Yellow-green, nearest to RHS 148A, and lightly suffused with greyed-brown, nearest to RHS N199A.

*Stipule.*—Position — A dry stipule is present on each side of the base of the petiole. Shape — Broad lanceolate. Apex — Aristate. Base — Broad cuneate. Aspect — Flattened on the upper side; otherwise rounded. Length — 2.6 cm. Width — 1.3 cm. Texture and luster, adaxial surface — Smooth, glabrous and matte. Texture and luster, abaxial surface — Smooth, glabrous and matte. Color, adaxial surface — Brown, nearest to RHS 200B. Color, abaxial surface — Brown, nearest to RHS 200A.

*Petiole.*—Length — 0.7 cm. Diameter — 0.55 cm. Strength — Strong. Texture — Smooth, glabrous and slightly glossy. Luster — Matte. Color, adaxial surface — Green, nearest to a mixture of NN137A and NN137B. Color, abaxial surface — Yellow-green, nearest to RHS 146A.

Inflorescence: No flowering has been observed to date.

Comparison with the parent plant: Plants of the new cultivar 'BAMBINO2' differ from the parent, *Ficus* 'Bambino' (U.S. Pat. No. PP9,323), in the following characteristics described in Table 1 below.

TABLE 1

| Characteristic | 'BAMBINO2' | 'Bambino' |
|---|---|---|
| Foliage size. | Smaller than 'Bambino' | Larger than 'BAMBINO2' |
| General coloration of the mature foliage. | Darker green. | Lighter green. |

Comparison with the closest known comparator:

Plants of the new cultivar 'BAMBINO2' differs from the commercial variety, *Ficus* sp. 'ESMINAUD' (Community Plant Variety Rights grant number 41449) in the following characteristics described in Table 2 below.

TABLE 2

| Characteristic | 'BAMBINO2' | 'ESMINAUD' |
|---|---|---|
| Abundance of foliage. | More abundant. | Less abundant. |
| Foliage attitude. | More relaxed. | More upright. |

TABLE 2-continued

| Characteristic | 'BAMBINO2' | 'ESMINAUD' |
|---|---|---|
| Foliage aspect. | Moderately concave; cupped. | Flat. |
| General coloration of the foliage. | Darker green. | Lighter green. |

That which is claimed is:

1. A new and distinct variety of *Ficus* plant named 'BAMBINO2', substantially as described and illustrated herein.

* * * * *